(12) United States Patent
Nose et al.

(10) Patent No.: US 11,000,242 B1
(45) Date of Patent: May 11, 2021

(54) METHODS AND SYSTEMS FOR COLLIMATORS OF A CT DETECTOR

(71) Applicant: GE Precision Healthcare LLC, Milwaukee, WI (US)

(72) Inventors: Katsumasa Nose, Tokyo (JP); Nicholas Konkle, Sussex, WI (US); Mark Adamak, Wauwatosa, WI (US); Jacob Biju, Niskayuna, NY (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 0 days.

(21) Appl. No.: 16/720,757

(22) Filed: Dec. 19, 2019

(51) Int. Cl.
*A61B 6/06* (2006.01)
*A61B 6/00* (2006.01)
*A61B 6/03* (2006.01)

(52) U.S. Cl.
CPC ............... *A61B 6/06* (2013.01); *A61B 6/032* (2013.01); *A61B 6/4208* (2013.01)

(58) Field of Classification Search
CPC .................................. A61B 6/032; A61B 6/06
See application file for complete search history.

(56) References Cited

U.S. PATENT DOCUMENTS

| | | | | |
|---|---|---|---|---|
| 4,710,947 A | * | 12/1987 | Klein | ............... A61B 6/06 211/85.13 |
| 2009/0067571 A1 | * | 3/2009 | Lacey | ............... A61B 6/032 378/19 |

* cited by examiner

*Primary Examiner* — David P Porta
*Assistant Examiner* — Fani Boosalis
(74) *Attorney, Agent, or Firm* — McCoy Russell LLP

(57) ABSTRACT

Various methods and systems are provided for an X-ray imaging system comprising an X-ray source, an X-ray detector array having a plurality of X-ray detecting elements configured to detect X-rays passing through an object configured to be scanned, a plurality of collimator plates positioned between the object to be scanned and the X-ray detector array, wherein one or more of the plurality of collimator plates comprises at least one bend at or in a region of a bottom end of the collimator plate, the bottom end facing the X-ray detecting elements of the X-ray imaging system. The X-ray imaging system may be a CT imaging system or other imaging system that includes an X-ray source and an X-ray detector.

20 Claims, 12 Drawing Sheets

METHODS AND SYSTEMS FOR COLLIMATORS OF A CT DETECTOR

FIELD

Embodiments of the subject matter disclosed herein relate to collimators for use in diagnostic imaging and, more particularly, collimators for a Computed Tomography (CT) detector of a CT imaging system.

BACKGROUND

CT detectors typically include a plurality of collimator plates for collimating X-ray beams such that collection of scattered X-rays on the X-ray detecting element is minimized. In a detector area shadowed by collimator plates, the X-ray detecting elements are only receiving scattered X-ray radiation. In order to prevent the collimator plates from shadowing the X-ray detecting elements, a grid plate is bonded onto the X-ray detecting elements. In this way, the shadow of the collimator plates is only covering the grid plate.

BRIEF DESCRIPTION

In one embodiment, an X-ray imaging system comprises a plurality of collimator plates, wherein each of the collimator plate comprises at least one bent portion at or in a region of the bottom end of the collimator plate facing X-ray detecting elements of the X-ray imaging system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of an X-ray imaging system including a plurality of collimator plates for collimating X-ray beams, wherein each of the collimator plates comprise at least a bent portion on a bottom end of the collimator plate facing X-ray detecting element of the X-ray imaging system. As introduced above, an X-ray imaging system includes a plurality of collimator plates to reduce X-ray beams scatter. As the collimator plates attenuate off-angle scattered X-rays, shadow of the collimator plates may be caused by X-ray defocusing. In order to prevent shadow of the collimator plates from entering the X-ray detecting element, a grid-like tungsten plate called a grid plate is bonded onto the X-ray detecting element. The grid plate receives the shadow of the collimator plates, and therefore minimizes noise caused by the shadow of collimator plates. The X-ray imaging system may be a CT imaging system or other imaging system that includes an X-ray source and an X-ray detector.

However, a width of each individual grid of the grid plate depends on tolerance of the collimator plate position, tolerance of the grid plate installation, and a relative positional error between the collimator plate and X-ray detecting element. Typically, the larger the tolerance/error, the wider the grid plate. As a result, the grid can be much wider than the thickness of the collimator plate, which leads to a reduced X-ray receiving area on the X-ray detecting element. In addition, the cost of installing the grid plate to the X-ray detecting element may be high.

In one example, an X-ray imaging system includes a plurality of collimator plates, wherein each of the plurality of collimator plates comprises at least a bend. In one example, the at least one bend may be position at or in a region of the bottom end of the collimator plate facing X-ray detecting element of the X-ray imaging system. By bending the bottom end of the collimator plate, for example, the bottom width of the collimator plate is increased, and the shadow of the collimator plates caused by X-ray is received by the bent portion. In this way, no grid plate is needed (or a reduced size grid plate may be used) to receive the shadow of the collimator plates. Further, since the collimator plate and the bent portion that receives the shadow of the collimator plates may be integrated, there is reduced positional deviation between the two. As a result, the area covering the X-ray detecting element can be reduced, leading to increased X-ray detecting efficiency. Further still, bending the collimator plate at or near the bottom end may increase rigidity of the collimator plate, therefore reducing the risk of collimator plate deformation due to a centrifugal force.

Figure 1:
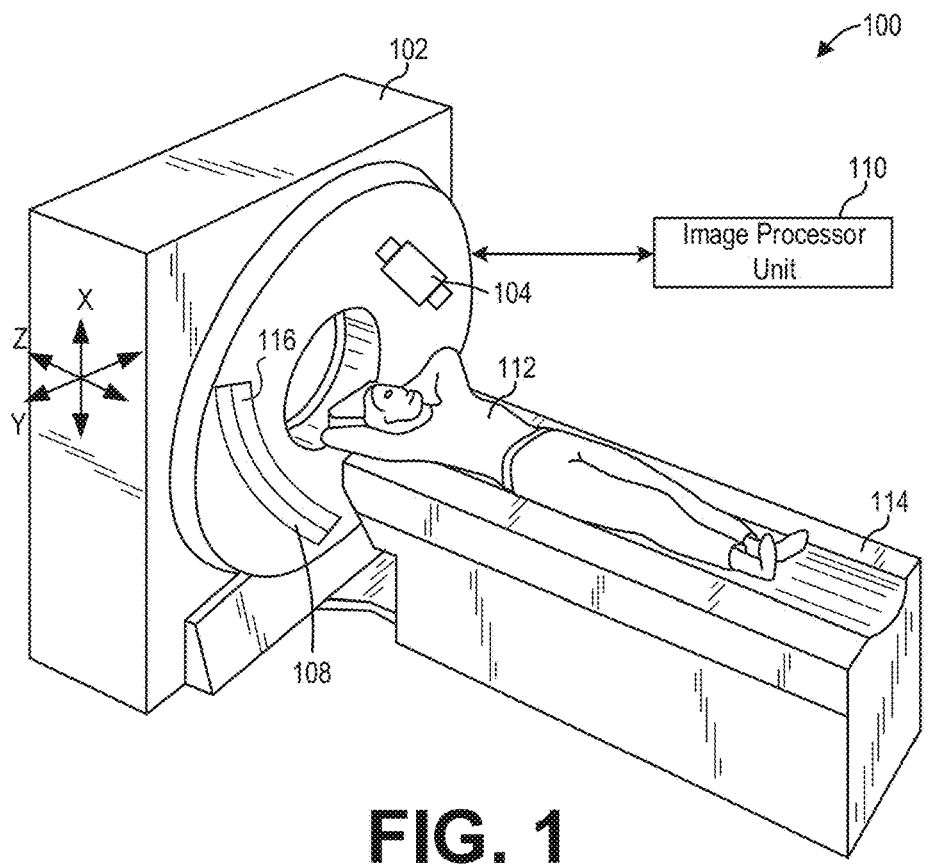
FIG. 1 shows a pictorial view of a CT imaging system that incorporates disclosed embodiments.

FIG. 1 illustrates an exemplary CT imaging system 100 configured for CT imaging. Particularly, the CT imaging system 100 is configured to image a subject 112 such as a patient, an inanimate object, one or more manufactured parts, industrial components, and/or foreign objects such as implants, stents, and/or contrast agents present within the body. In one embodiment, the CT imaging system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beam 106 towards a collimator 116 and a detector array 108 positioned on the opposite side of the gantry 102. Although FIG. 1 depicts only a single X-ray source 104, in certain embodiments, multiple X-ray sources and may be employed to project a plurality of X-ray radiation beams towards multiple collimators and detectors for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and X-ray detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT imaging system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an X-ray radiation source projects a cone-shaped beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of X-ray detecting elements. The intensity of the attenuated X-ray radiation beam received at the detector array is dependent upon the attenuation of an X-ray radiation beam by the object. Each X-ray detecting element of the array produces a separate electrical signal that is a measurement of the X-ray beam attenuation at the detector location. The attenuation measurements from all the X-ray detecting elements are acquired separately to produce a transmission profile.

In some CT imaging systems, the radiation-ray source and the detector array are rotated with a gantry within the imaging plane and around the object to be imaged such that an angle at which the X-ray radiation beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Figure 2:
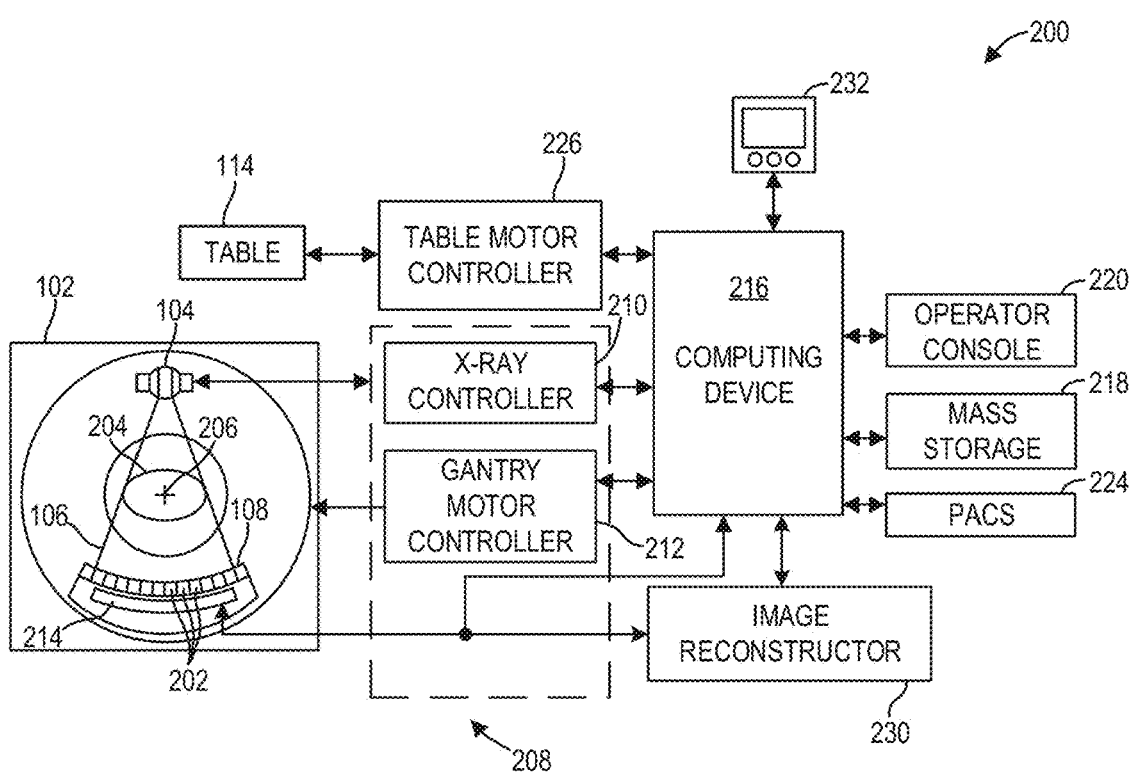
FIG. 2 shows a block schematic diagram of the system illustrated in FIG. 1.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of X-ray detecting elements 202 that together sense the X-ray radiation beams 106 that pass through the subject 204 (such as a patient) to acquire corresponding projection data. Accordingly, in one embodiment, the detector array 108 is fabricated in a multi-slice configuration including the plurality of rows of cells or X-ray detecting elements 202. In such a configuration, one or more additional rows of the X-ray detecting elements 202 are arranged in a parallel configuration for acquiring the projection data.

In certain embodiments, the X-ray imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections.

In some examples, the individual detectors or X-ray detecting elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the X-ray detecting elements 202 and convert the analog data to digital signals for subsequent processing. The DAS 214 may be further configured to selectively aggregate analog data from a subset of the X-ray detecting elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the X-ray detecting elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
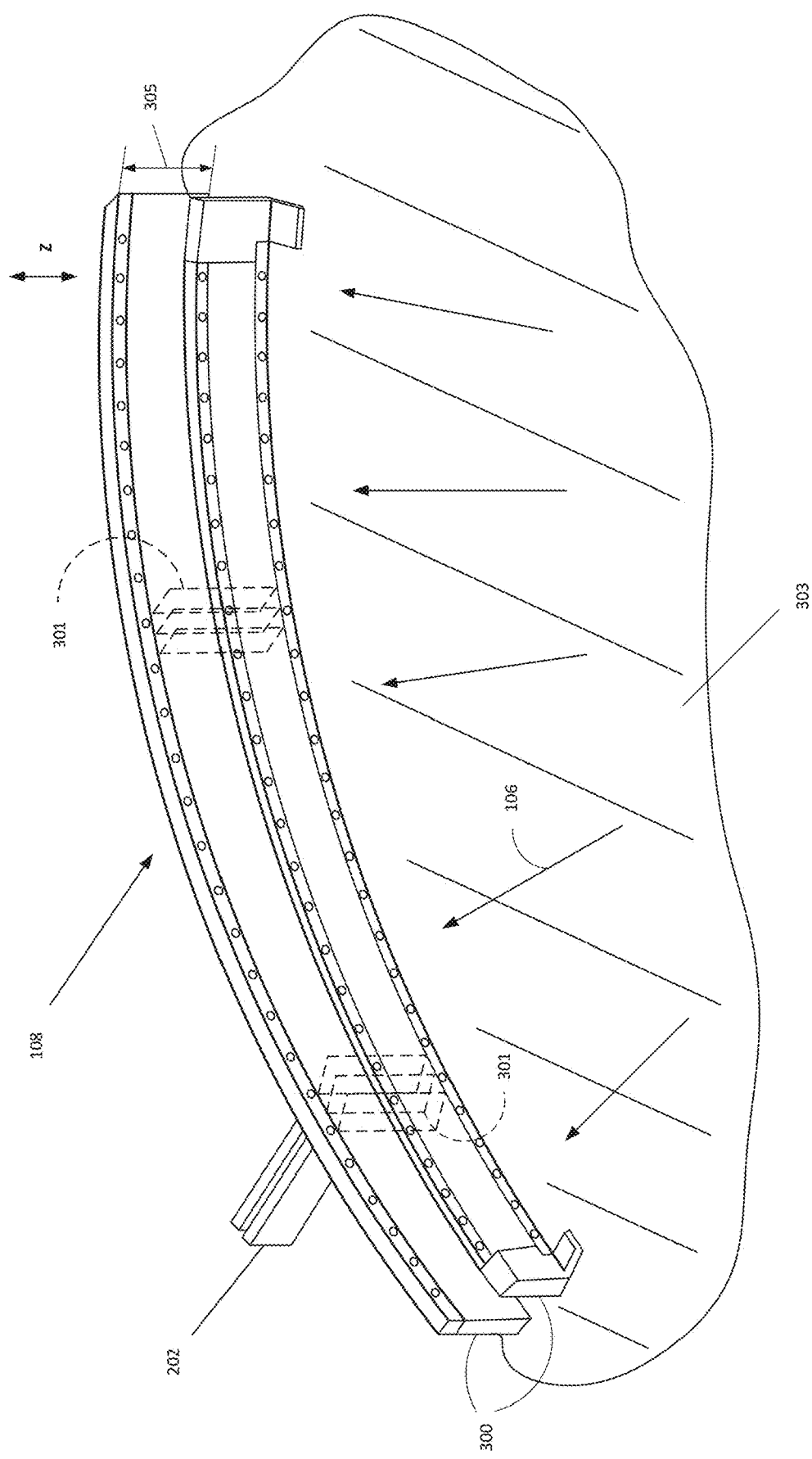
FIG. 3 shows a perspective view of one embodiment of a CT detector array.

FIG. 3 shows a typical CT detector array 108 including rails 300 having collimator plates 301 placed therebetween. The collimator plates 301 are positioned to collimate X-rays 106 before such X-ray beams impinge upon, for instance, X-ray detecting elements 202 positioned on detector array 108 as shown in FIGS. 1-2. Rails 300 are mounted to a plate 303 that is vertically mounted in gantry 102. Z-axis therefore extends orthogonal to plate 303 such that rails 300 extend axially and at a distance 305 from plate 303. Thus, as detectors grow in Z-direction, so too does cantilever distance 305.

Figure 4:
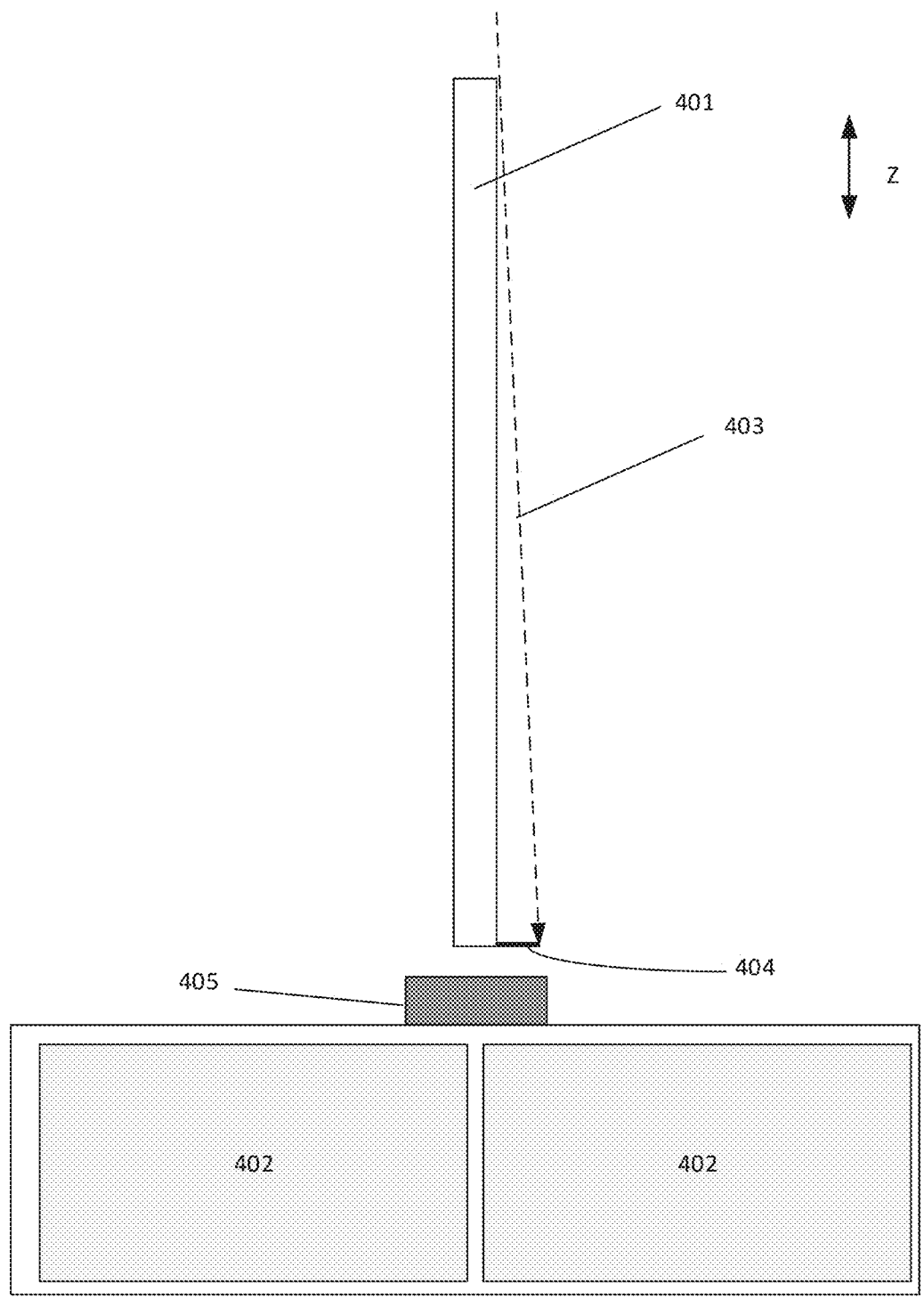
FIG. 4 shows a cross-sectional view of a collimator plate and X-ray detecting elements of a CT detector array previously implemented.
Figure 5A:
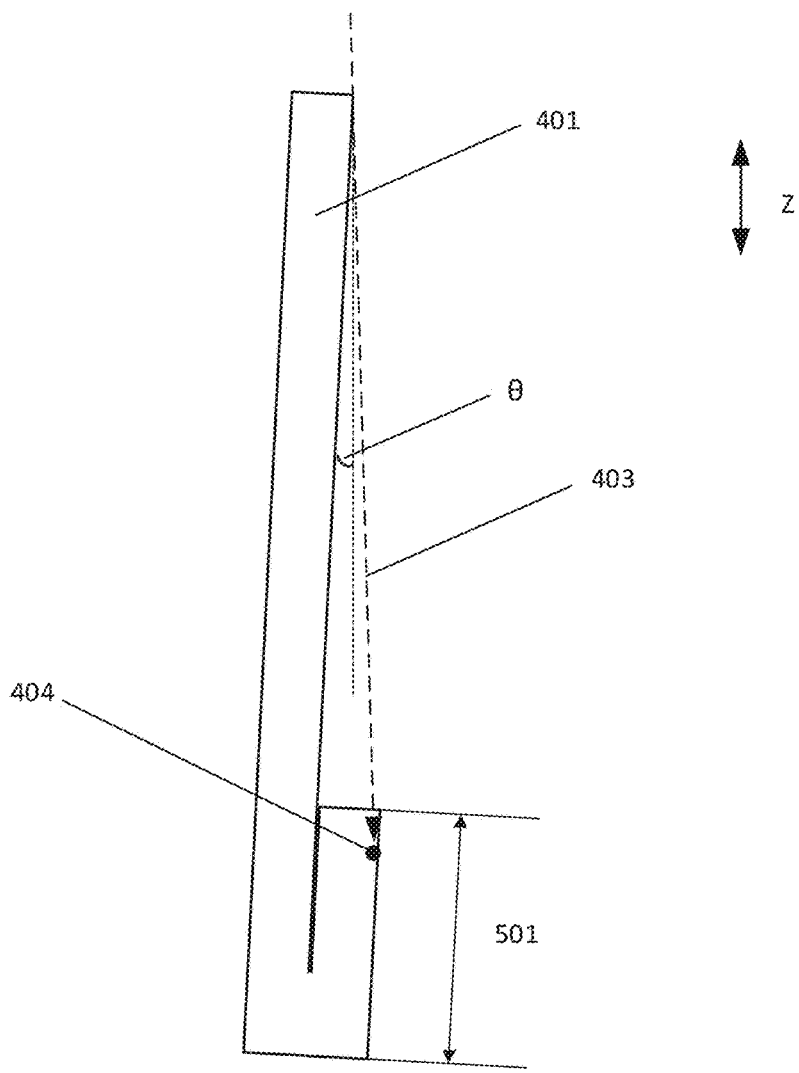
FIG. 5A illustrates a first exemplary configuration with a tilted collimator plate and a bent portion at the bottom end of the collimator plate.
Figure 5A:
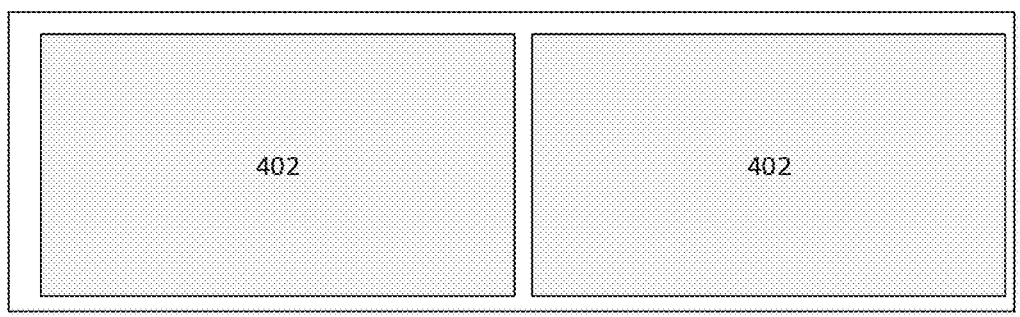
Figure 5B:
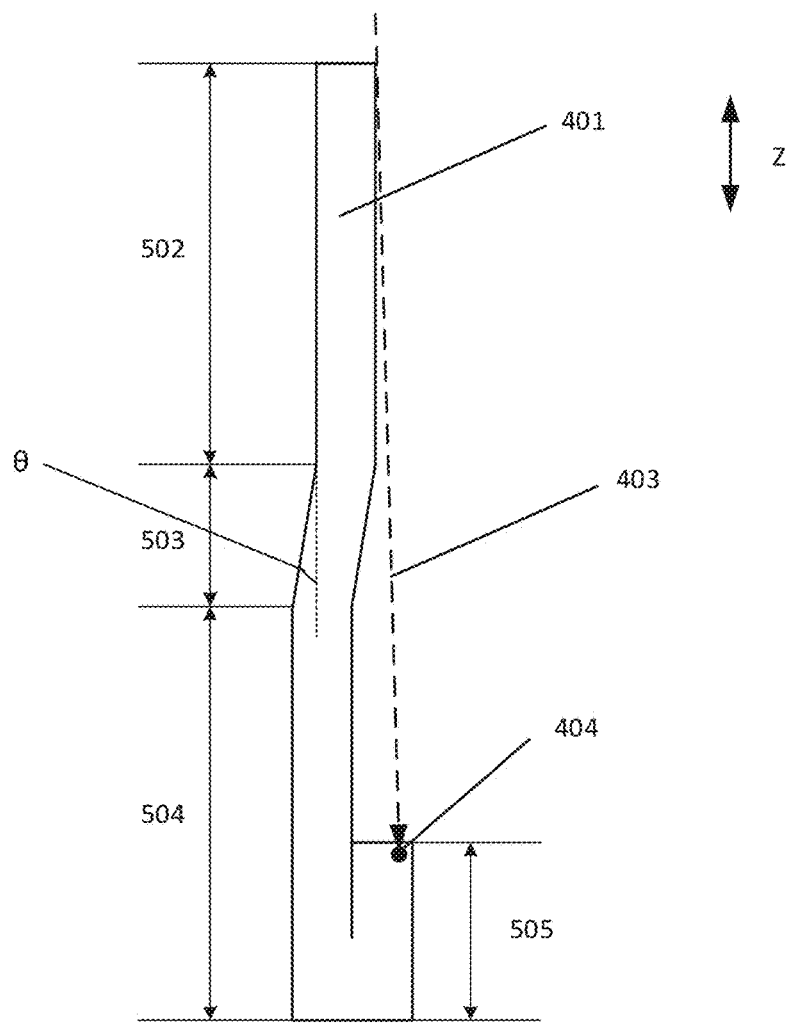
FIG. 5B illustrates a second exemplary configuration with a collimator plate comprising two bends along the collimator plate and one bent at the bottom end of the collimator plate.
Figure 5B:
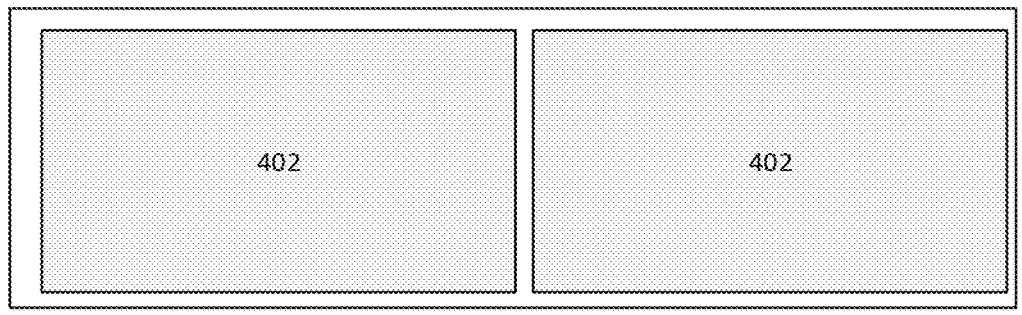
Figure 5C:
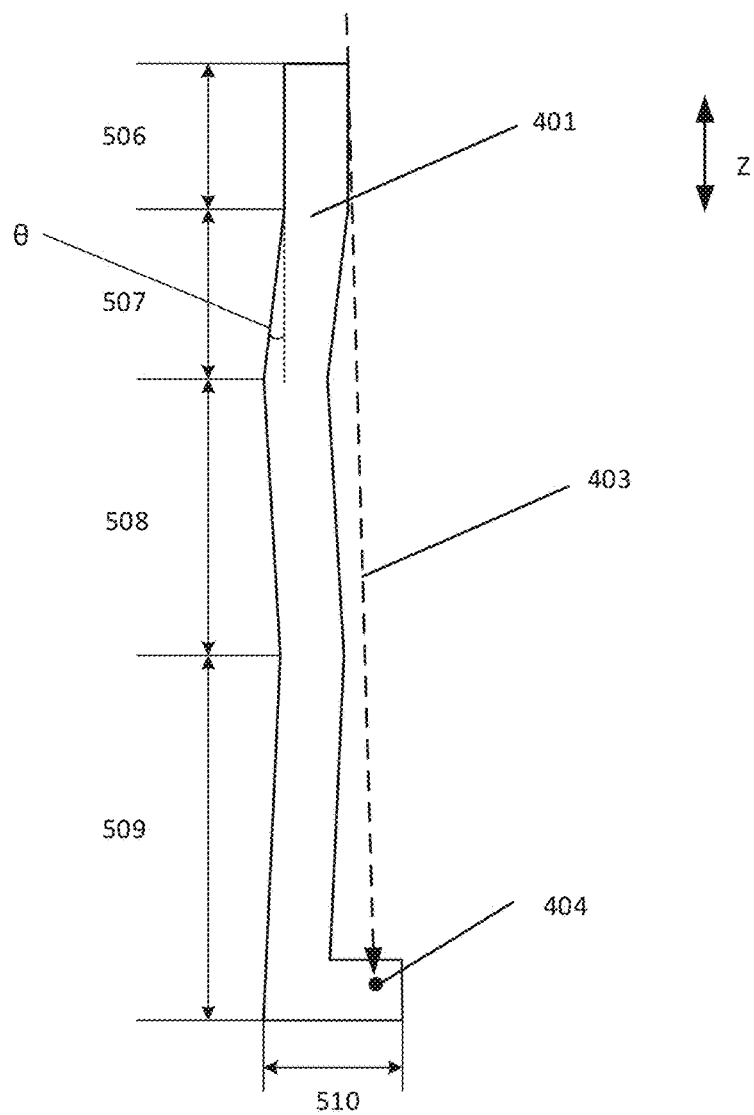
FIG. 5C illustrates a third exemplary configuration with a collimator plate comprising three bends along the collimator plate and one bend at the bottom end of the collimator plate.
Figure 5C:
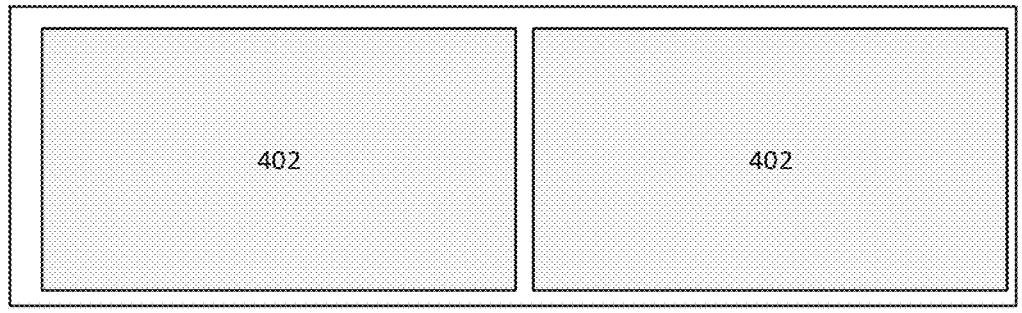
Figure 5D:
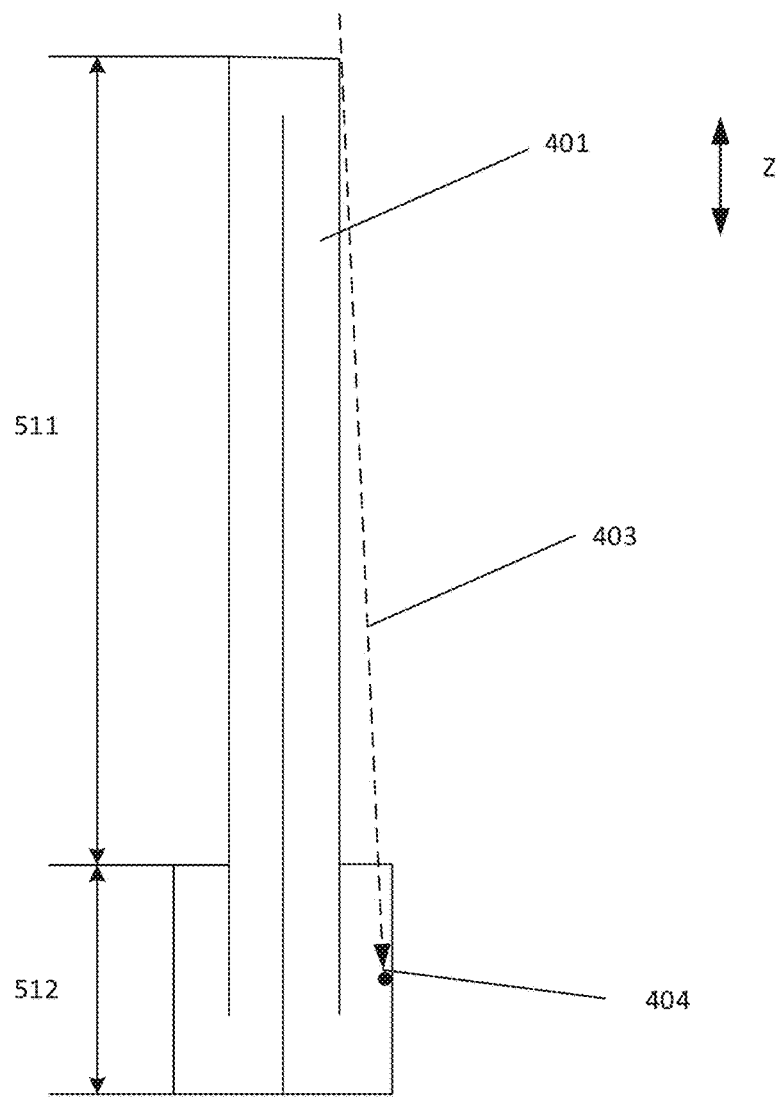
FIG. 5D illustrates a fourth exemplary configuration with a bent collimator plate comprising one hemming fold at the top end and two hemming folds at the bottom end.
Figure 5D:
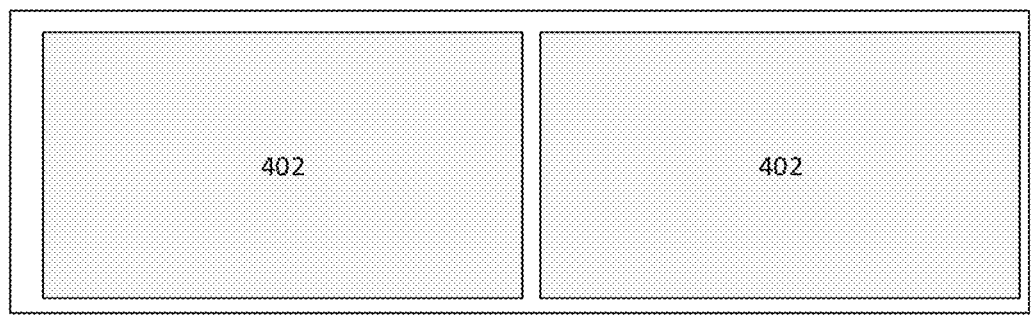
Figure 5E:
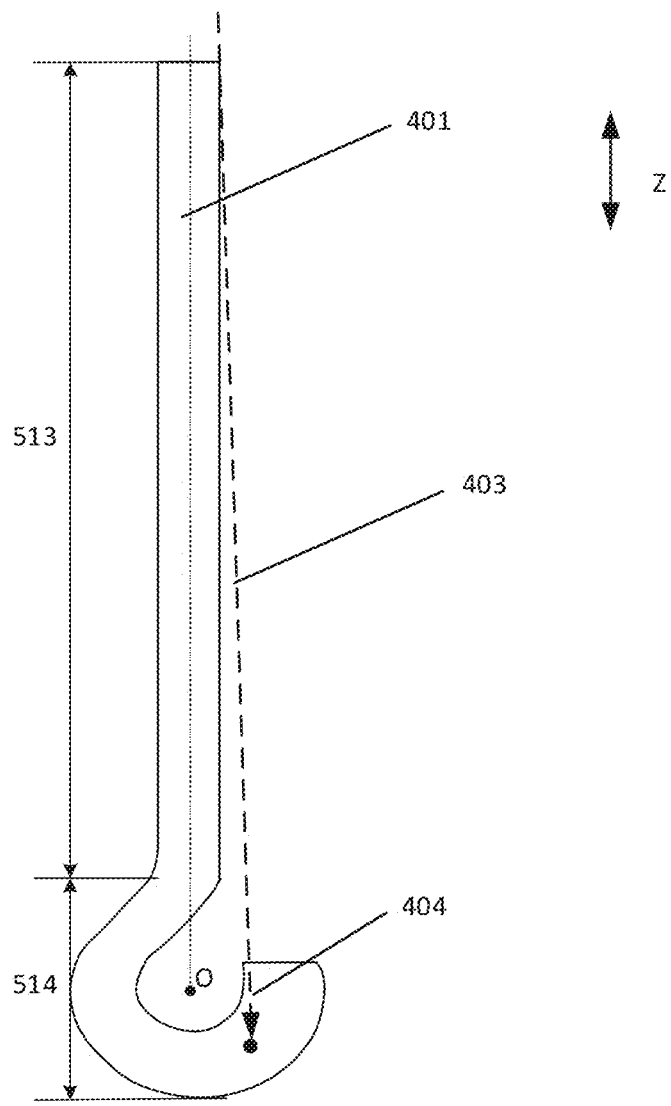
FIG. 5E illustrates a fifth exemplary configuration with a bulb-shaped bend at the bottom end of the collimator plate.
Figure 5E:
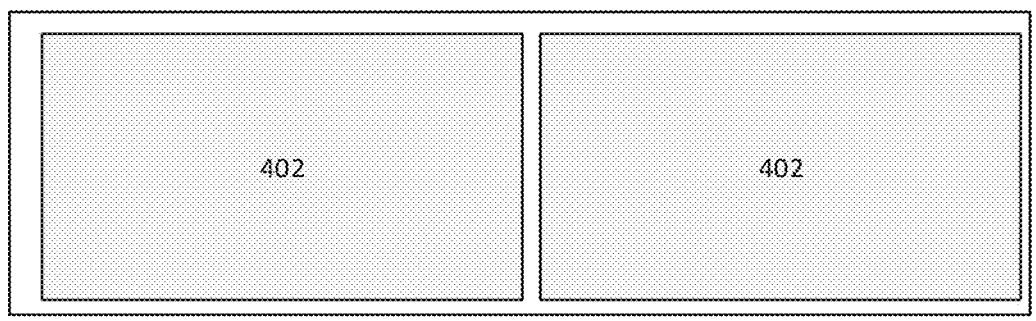
Figure 5F:
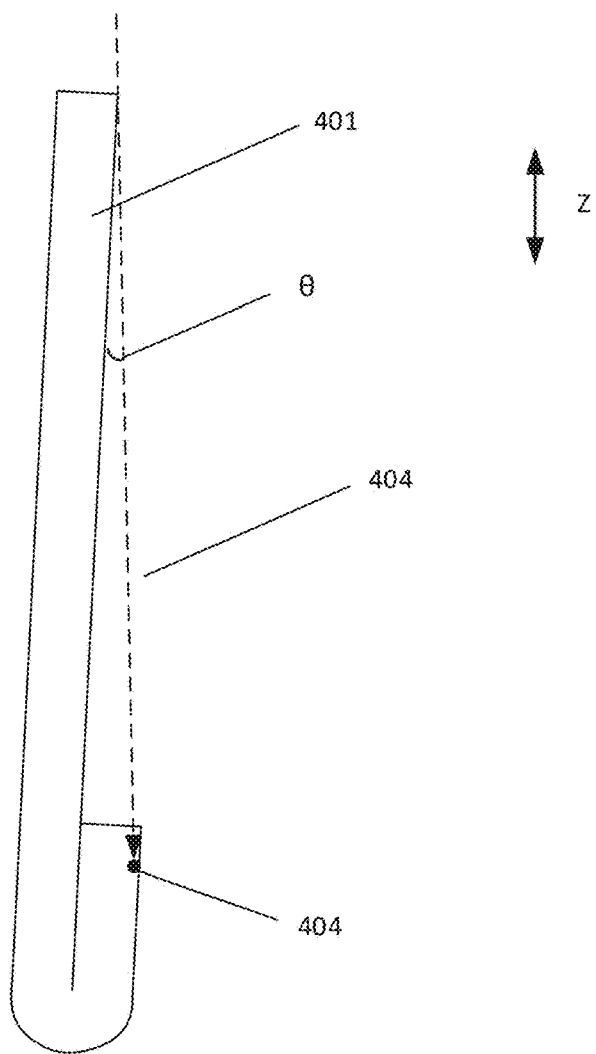
FIG. 5F illustrates a sixth exemplary configuration with a tilted collimator plate and a bent portion at the bottom end of the collimator plate, wherein the corner of the bent portion is curved.
Figure 5F:
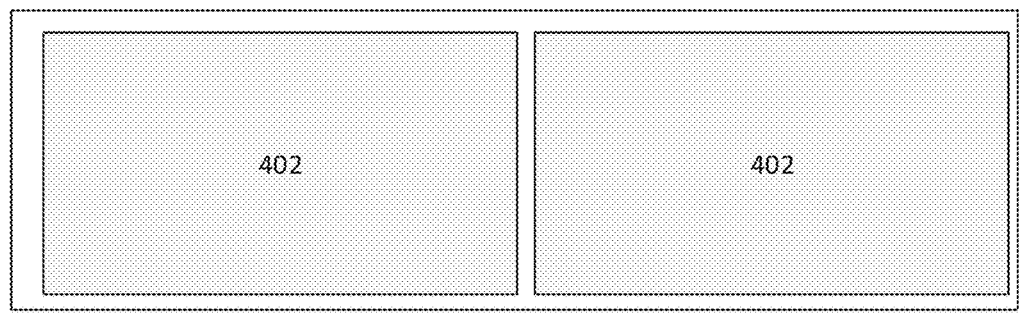
Figure 5G:
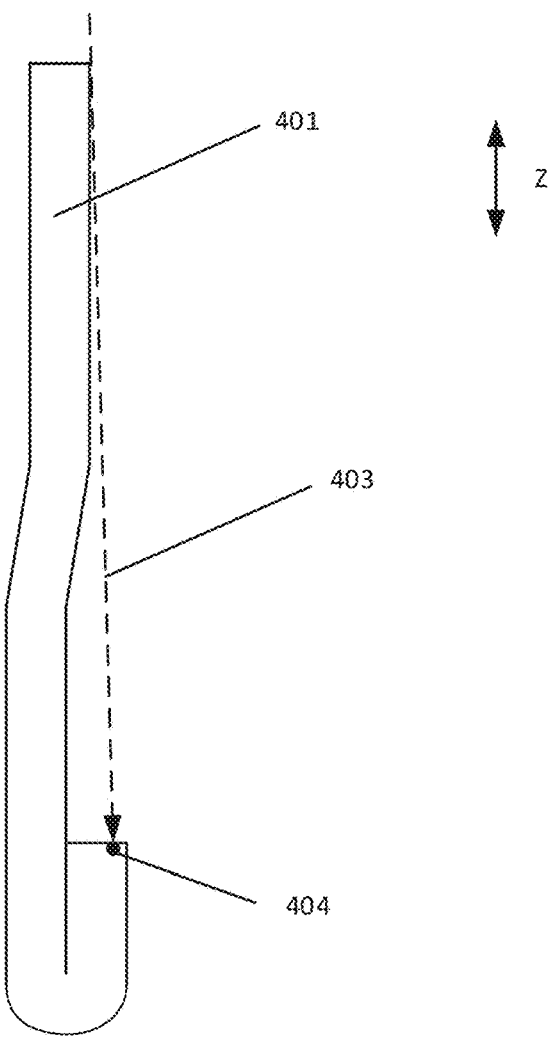
FIG. 5G illustrates a seventh exemplary configuration with a collimator plate with bends in an upper portion and a bent portion at the bottom end of the collimator plate, wherein the corner of the bent portion is curved.
Figure 5G:
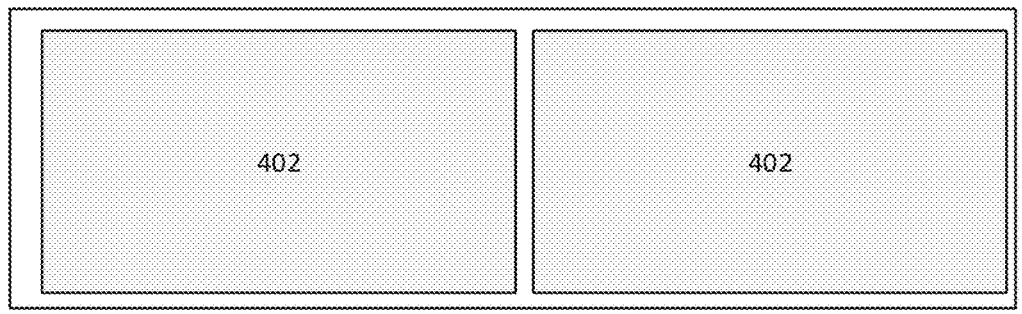
Figure 5H:
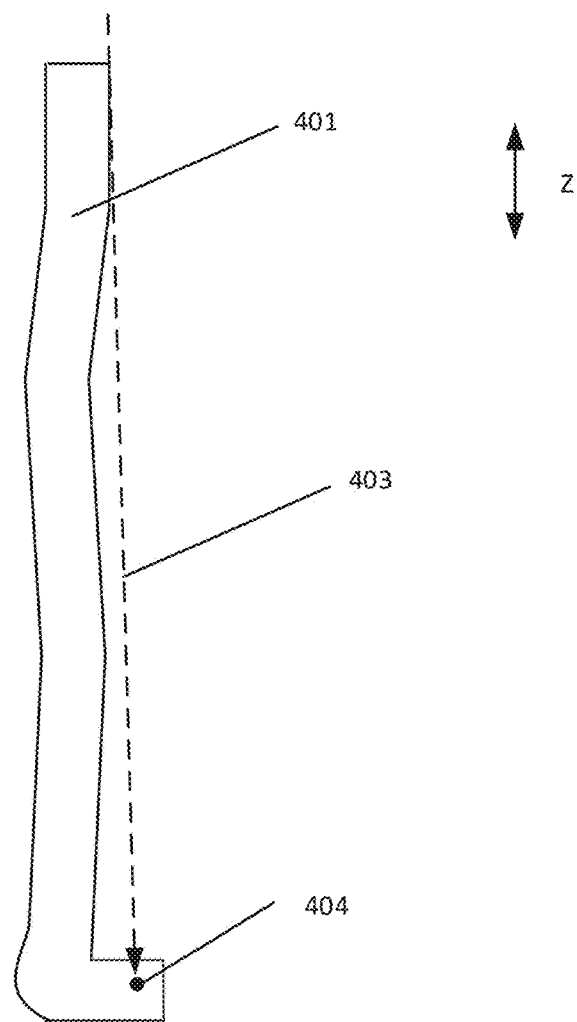
FIG. 5H illustrates an eighth exemplary configuration with a collimator plate with bends in an upper portion and a bent portion at the bottom end of the collimator plate, wherein the corner of the bottom bent portion is curved.
Figure 5H:
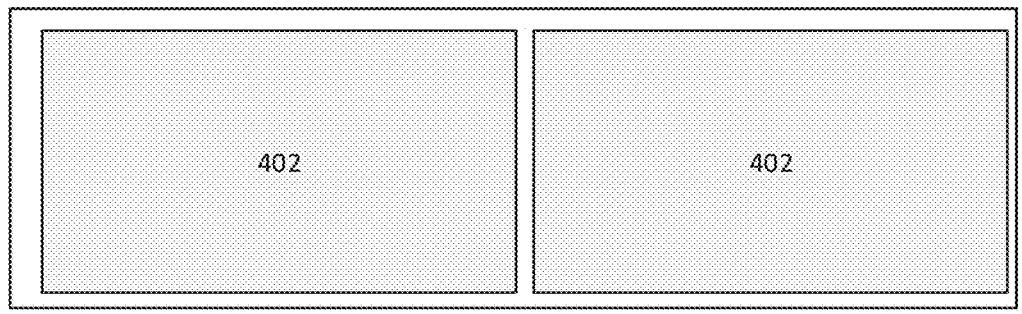
Figure 5I:
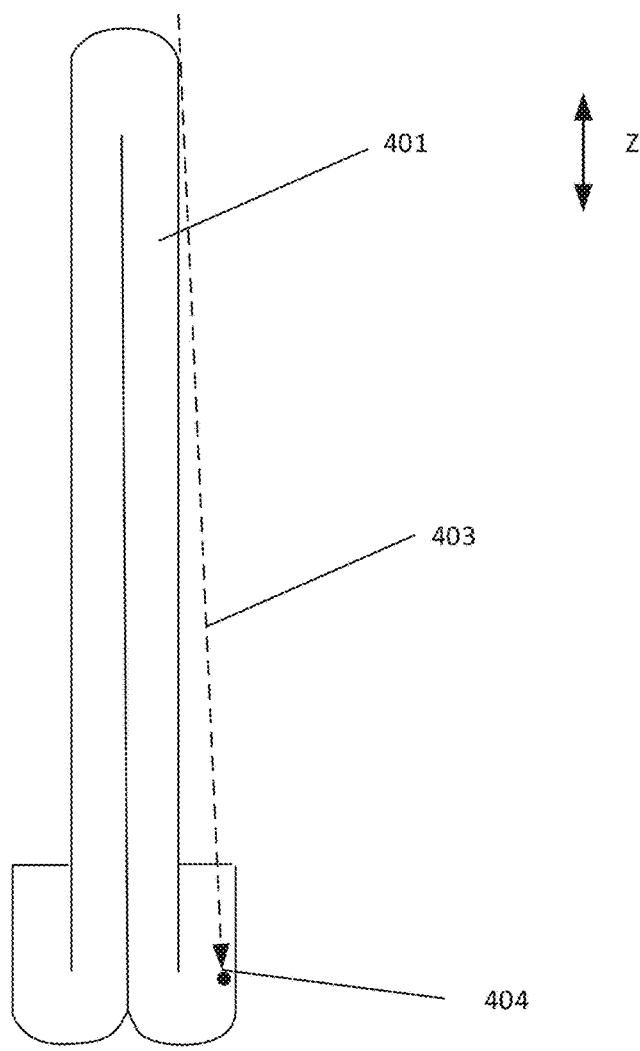
FIG. 5I illustrates a ninth exemplary configuration with a bent collimator plate comprising one hemming fold at the top end and two hemming folds at the bottom end, wherein the corners of the hemming folds are curved.
Figure 5I:
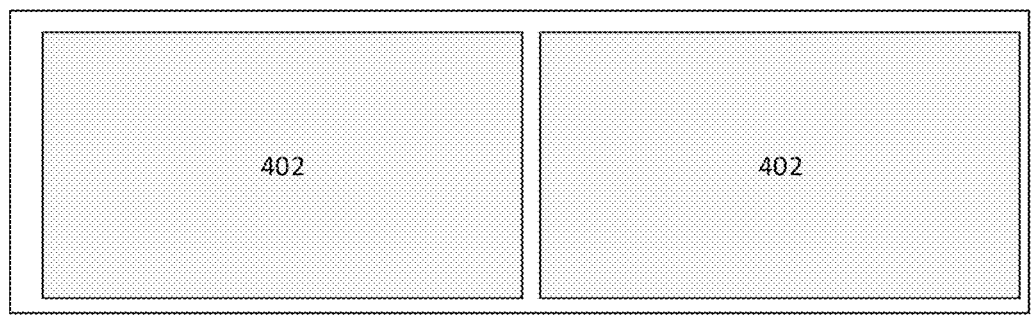

FIGS. 4-5I show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Referring to FIG. 4, a collimator plate and X-ray detecting elements of a CT detector array previously implemented is shown. The CT detector array comprises a collimator plate 401, two X-ray detecting elements 402, an illustrated X-ray beam 403, shadow 404 of the collimator plate, and a grid plate 405 mounted on the X-ray detecting elements 402. As shown in FIG. 4, the collimator plate 401 causes a shadow 404. In the shadowed area, the X-ray detecting elements are only able to receive scattered X-ray radiation. In order to prevent the collimator plate 401 from shadowing the X-ray detecting elements 402, a grid plate 405 is coupled to the X-ray detecting elements 402. In this way, the shadow 404 is only covering the grid plate 405. In order to prevent the shadow 404 from covering the X-ray detecting elements 402, the grid plate 405 has to be at least as wide as the width of the collimator plate 401 combined with the shadow 404. However, due to tolerance of the collimator plate's position, tolerance of the grid plate 405 installation, and a relative positional error between the collimator plate 401 and the X-ray detecting elements 402, the actual width of the grid plate needs to be wider than the combined width of the collimator plate 401 and the shadow 404. As a result, less X-rays are received by the X-ray detecting elements 402, leading to reduced X-ray detecting efficiency.

Referring now to FIGS. 5A-5I, various examples of the X-ray detecting system of present disclosure are shown. As shown in FIG. 5A, the collimator plate 401 is tilted at an angle θ relative to Z-direction. The angle θ is greater than 0 and less than 3 degrees. In one example, the angle θ is 2 degrees. At the bottom portion of the collimator plate 401, the collimator plate 401 is bent at approximately 180 degrees, which doubles the width of the bottom end of the collimator plate 401. The bent portion 501 is a part of the collimator plate 401, and the interior side of the bent portion 501 is in face-sharing contact with unbent portion of the collimator plate 401. As shown in FIG. 5A, when the collimator plate 401 is tilted clockwise, the bent portion 501 is placed on the right side of the collimator plate 401. Similarly, if the collimator plate is tilted counterclockwise, the bent portion 501 is then placed on the left side of the collimator plate 401. As such, the shadow 404 is received by the bent portion 501 at the bottom of the collimator plate 401.

FIG. 5B shows a second exemplary configuration with the collimator plate 401, wherein a first portion 502 of the collimator plate 401 is substantially parallel to Z-direction, a second portion 503 of the collimator plate 401 comprising two sequential bends, with a first bend away from Z-direction at an angle θ that is greater than 0 and less than 3 degrees, and a second bend towards Z-direction that is greater than −3 and less than 0 degree; and a third portion 504 of the collimator plate 401 positioned in Z-direction, the first portion 502 is on top of the second portion 503, the second portion 503 is on top of the third portion 504. Further, a bent portion 505 is at the bottom end of the third portion 504 at approximately 180 degrees, which doubles the width of the bottom end of the collimator plate 401. The bent portion 505 is a part of the collimator plate 401, and the interior side of the bent portion 505 is in face-sharing contact with the third portion 504. As shown in FIG. 5B, when the second portion 503 is bent toward the left side of Z-direction, the bent portion 505 is arranged on the right side of the collimator plate 401. Similarly, if the second portion 503 is bent toward the right side of Z-direction, the bent portion 505 is then placed on the left side of the collimator plate 401. The bent portion 505 shorter than the third portion 504. As such, the shadow 404 is received by the bent portion 505 near the bottom of the collimator plate 401.

FIG. 5C shows a third exemplary configuration with the collimator plate 401, wherein a first portion 506 is substantially positioned in Z-direction, a second portion 507 is bent away from Z-direction at an angle θ that is greater than 0 and less than 1 degree, a third portion 508 is bent at an angle opposite to angle θ relative to Z-direction, a fourth portion 509 is bent in the same direction as the second portion 507, and a fifth portion 510 at the bottom end of the fourth portion 509 is bent to be parallel with the X-ray detecting element array 402, which increases the width of bottom end of the collimator plate 401. The first portion 506 is on top of the second portion 507, the second portion 507 is on top of the third portion 508, and the third portion 508 is on top of the fourth portion 509. The length of the fifth portion 510 is approximately twice the width of the collimator plate 410. As shown in 5C, when the second and fourth portions 507 and 509 are bent toward the left side of Z-direction, the fifth portion 510 is bent toward the right side of the collimator plate 401. Similarly, if the second and fourth portions 507 and 509 are bent toward the right side of Z-direction, the fifth portion 510 is bent toward the left side of the collimator plate 401. As such, the shadow 404 is received by the fifth portion 510 at the bottom end of the collimator plate 401.

FIG. 5D shows a fourth exemplary configuration with the collimator plate 401, where a first portion 511 of the collimator plate 401 comprises a hemming fold on top, and a second portion 512 of the collimator plate 401 comprises two hemming folds at the bottom, one on the bottom right side and the other on the bottom left side. In the first portion 511, the collimator plate 401 is folded approximately 180 degrees so that the left and right parts of the collimator plate 401 are in face-sharing contact with each other, the left and right parts of the collimator plate 401 having the same length. In bottom regions of the left and right parts of the collimator plate 401, the left and right parts of the collimator plate 410 are folded outwards, wherein a bottom left part of the collimator plate 401 is bent clockwise until it is in face-sharing contact with the left part of the collimator plate 401, and a bottom right part of the collimator plate 401 is bent counterclockwise until it is in face-sharing contact with the right part of the collimator plate 401. The collimator plate 401 is positioned substantially in Z-direction, and the first portion 511 is on top of the second portion 512. The hemming folds increase the width of the bottom end of the collimator plate 401. As such, the shadow 404 is received by the hemming folds in the second portion 512 of the collimator plate 401.

FIG. 5E shows a fifth exemplary configuration with the collimator plate 401, comprising a first portion 513 positioned in Z-direction, and a second portion 514 with bulb-shaped bent at the bottom end of the collimator plate 401. The diameter of the second portion 514 is at least twice the width of the collimator plate 401. The bulb-shaped bend in the second portion 514 increases the width of the bottom end of the collimator 401. Further, a center O of the bulb-shaped bend lies on a central axis of the collimator plate 401. As such, the shadow 404 is received by the bulb-shaped bend of the collimator plate 401.

FIG. 5F shows a sixth exemplary configuration that is similar to FIG. 5A, wherein the corner of the bend at the bottom of the collimator plate 401 is curved.

FIG. 5G shows a seventh exemplary configuration that is similar to FIG. 5B, wherein the corner of the bend at the bottom of the collimator plate 401 is curved.

FIG. 5H illustrates an eighth exemplary configuration that is similar to FIG. 5C, wherein the corner of the bend at the bottom of the collimator plate 401 is curved.

FIG. 5I illustrates a ninth exemplary configuration that is similar to FIG. 5D, wherein the corners of the hemming folds at the bottom of the collimator plate 401 are curved.

Conventional X-ray imaging systems include a grid plate bonded onto the X-ray detecting element in order to receive shadows of the collimator plates caused by attenuation of X-ray due to misaligned or varied collimator plate. However, as explained above, a grid width of the grid plate depends on tolerance of the collimator plate position, tolerance of the grid plate installation, and a relative positional error between the collimator plate and X-ray detecting element. As a result, the grid typically needs to be much wider than the thickness of the collimator plate, which leads to reduced X-ray receiving area on the X-ray detecting element. In addition, grid plate installation is expensive.

The inventors recognize that it may be desirable to eliminate grid plate in an X-ray imaging system. Therefore, the present disclosure aims to provide an X-ray detecting system without a grid plate installed on the X-ray detecting element by using the collimator plates to catch the collimator plate shadows. In one embodiment, an X-ray imaging system includes a plurality of collimator plates, wherein each of the plurality of collimator plates comprises at least a bend at the bottom end of the collimator plate facing X-ray detecting elements of the X-ray imaging system.

By bending the bottom end of the collimator plate, the bottom width of the collimator plate is increased, and the collimator shadow is determined by the bend, not by the top or misaligned sections of the collimator plate that has higher variability with X-ray focal spot motion. In this way, present disclosure achieves the technical effect of an X-ray imaging system without a grid plate, resulting in minimized area covering the X-ray detecting element, higher X-ray detecting efficiency, and lower system cost. Further, the bent bottom of the collimator plate increases rigidity of the collimator plates, therefore reduces the risk of collimator plate deformation due to a centrifugal force.

As used herein, an element recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
   an X-ray source;
   an X-ray detector array having a plurality of X-ray detecting elements configured to detect X-rays passing through an object configured to be scanned; and
   a plurality of collimator plates positioned between the object to be scanned and the X-ray detector array;

wherein one or more of the plurality of collimator plates comprises at least one bend at or in a region of a bottom end of each collimator plate, the bottom end facing the X-ray detector array of the X-ray imaging system.

2. The X-ray imaging system of claim 1, wherein each of the plurality of collimator plates is positioned perpendicularly to the X-ray detector array.

3. The X-ray imaging system of claim 2, wherein each of the plurality of collimator plates comprises one hemming fold at a top end of the collimator plate, and the at least one bend comprises two hemming folds in a bottom region of the collimator plate.

4. The X-ray imaging system of claim 3, wherein the hemming fold is a U-shape fold.

5. The X-ray imaging system of claim 1, wherein each of the plurality of collimator plates is positioned at an angle θ relative to an axis that is perpendicular to the X-ray detector array, the angle θ is greater than 0 and less than 3 degrees.

6. The X-ray imaging system of claim 5, wherein an angle of the at least one bend at the bottom end of the collimator plate is between 90 to 180 degrees.

7. The X-ray imaging system of claim 1 wherein each of the plurality of collimator plates comprises at least two bends in a first portion of the collimator plate, and one bend at the bottom end of a second portion of the collimator plate, the first portion configured to receive an X-ray beam before the second portion.

8. The X-ray imaging system of claim 7, wherein the at least two bends in the first portion of the collimator plate are positioned at an angle greater than 0 and less than 3 degrees, and an angle of the one bend at the bottom end of the second portion of the collimator plate is between 90 to 180 degrees.

9. The X-ray imaging system of claim 1, wherein the at least one bend at the bottom end of the collimator plate is curved.

10. The X-ray imaging system of claim 9, wherein the at least one bend at the bottom end of the collimator plate forms a round, bulb-shaped bend, wherein a diameter of the bulb-shaped bend is at least twice the width of the collimator plate, and a center of the bulb-shaped bend lies on a central axis of the collimator plate.

11. A method of assembling a CT detector, comprising:
arranging a plurality of collimator plates in a y-z plane between two rails of the CT detector to form an array of collimator plates;
arranging a plurality of X-ray detecting elements in a y-z plane on an outer rail of the two rails to form an array of X-ray detecting elements; and
mounting the two rails to a support structure;
wherein the method further includes bending a bottom region of the collimator plate, the bottom region of the collimator plate facing the array of X-ray detecting elements.

12. The method of claim 11, further comprising bending the bottom region of the collimator plate includes bending the bottom region of the collimator plate to an angle between 90 to 180 degrees.

13. The method of claim 12, further comprising making the angle curved.

14. The method of claim 11, further comprising arranging each of the plurality of collimator plates substantially perpendicular to the array of X-ray detecting elements.

15. The method of claim 14, further comprising bending each of the plurality of collimator plates above the bottom region of the collimator plates, each bend above the bottom region at angles greater than −3 and less than 0 degree relative to an axis that is perpendicular to the array of X-ray detecting elements.

16. The method of claim 15, further comprising bending each of the plurality of collimator plates up to three times above the bottom region.

17. The method of claim 11, further comprising positioning the plurality of X-ray detecting elements on the outer rail by use of pins.

18. An X-ray radiation detection apparatus for use in an X-ray radiation tomography apparatus, comprising:
a detector array in which a plurality of X-ray detecting elements is positioned on an outer rail of two curved rails, the detector array arranged substantially in a fan-angle direction; and
a plurality of collimator plates positioned between the two curved rails;
wherein each of the plurality of collimator plates comprises at least one bend at the bottom end of the collimator plate, the bottom end of the collimator plate facing the detector array.

19. The X-ray radiation detection apparatus of claim 18, wherein the at least one bend at the bottom end of the collimator plate is between 90 to 180 degrees relative to the collimator plate.

20. The X-ray radiation detection apparatus of claim 18, wherein a corner of the at least one bend at the bottom end of the collimator plate is curved.

* * * * *